US008262598B2

(12) United States Patent  (10) Patent No.: US 8,262,598 B2
Smits  (45) Date of Patent: Sep. 11, 2012

(54) FRAME FOR A HYPEREXTENSION BRACE

(75) Inventor: Jan Smits, Helmond (NL)

(73) Assignee: Camp Scandinavia AB, Helsingborg (SE)

(*) Notice: Subject to any disclaimer, the term of this patent is extended or adjusted under 35 U.S.C. 154(b) by 797 days.

(21) Appl. No.: 12/304,043

(22) PCT Filed: Jun. 11, 2007

(86) PCT No.: PCT/EP2007/055725
§ 371 (c)(1),
(2), (4) Date: Dec. 9, 2008

(87) PCT Pub. No.: WO2007/144328
PCT Pub. Date: Dec. 21, 2007

(65) Prior Publication Data
US 2010/0234783 A1  Sep. 16, 2010

(30) Foreign Application Priority Data
Jun. 12, 2006 (EP) .................... 06115288

(51) Int. Cl.
A61G 15/00 (2006.01)
A61F 5/37 (2006.01)
A61F 5/24 (2006.01)
A61F 5/28 (2006.01)
A61F 5/00 (2006.01)

(52) U.S. Cl. .......... 602/19; 128/DIG. 23; 128/845; 128/846; 128/98.1; 128/99.1; 602/5; 602/16; 602/18; 602/32; 602/33; 602/34; 602/35; 602/36; 602/38; 606/240; 606/241

(58) Field of Classification Search ........... 128/DIG. 23, 128/845, 846, 98.1, 99.1; 602/5, 16, 18, 602/19, 32–36, 38; 606/240, 241
See application file for complete search history.

(56) References Cited

U.S. PATENT DOCUMENTS

| 2,835,247 | A |   | 5/1958  | Stabholc |
| 3,220,407 | A |   | 11/1965 | Connelly |
| 4,987,885 | A | * | 1/1991  | Shtabholz ............ 606/241 |
| 6,010,472 | A |   | 1/2000  | Schiller |
| 6,210,354 | B1 |  | 4/2001  | Ousdal |

FOREIGN PATENT DOCUMENTS

| DE | 19607718 A1 | 9/1996 |
| EP | 0319224 A2  | 6/1989 |
| GB | 714733 A    | 9/1954 |

* cited by examiner

Primary Examiner — Patricia Bianco
Assistant Examiner — Nihir Patel
(74) Attorney, Agent, or Firm — Volpe and Koenig, P.C.

(57) ABSTRACT

A hyperextension brace with a frame construction has adjustable upper and lower supports as well as adjustable side members. The frame comprises a sub-clavicula support and a pelvic and pubic support connected by side members. The height of the side members and the width of the sub-clavicula support and the pubic support are adjustable by using non-rotational telescopic and lockable connections. The sub-clavicula support may be connected by a turnbuckle screw arrangement to the side members. The frame may be made of composite material, suitably a polymer reinforced by glass fiber and/or carbon fiber. All adjustments may be made without requiring any tools.

20 Claims, 4 Drawing Sheets

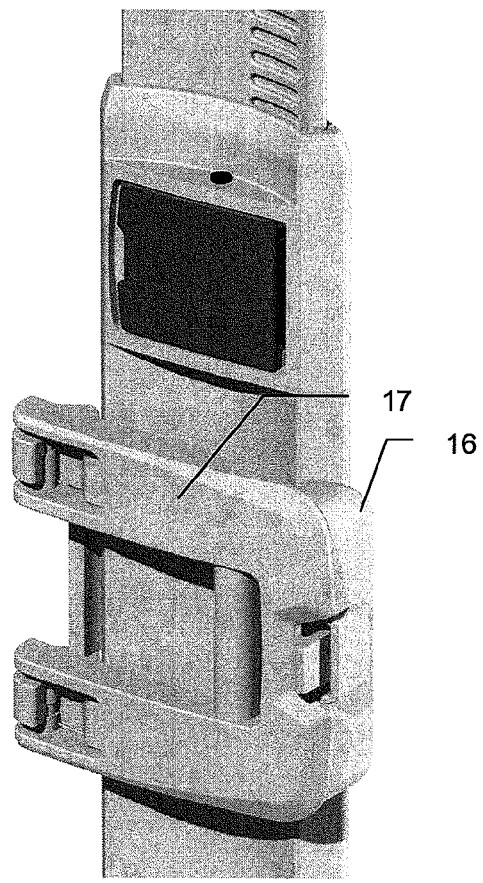
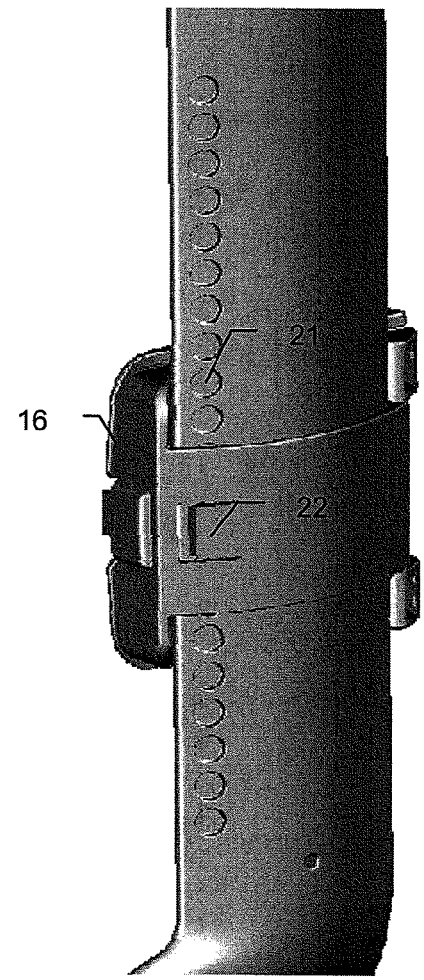
FIG 9
FIG 10

FRAME FOR A HYPEREXTENSION BRACE

FIELD OF THE INVENTION

The present invention relates to a hyperextension brace with a frame construction having adjustable upper and lower supports as well as adjustable side members. All adjustments may be made without requiring any tools. Preferably, the frame is made of composite material.

BACKGROUND OF THE INVENTION

Hyperextension braces are previously known devices as may be seen for example from U.S. Pat. No. 3,220,407 and U.S. Pat. No. 6,010,472. Hyperextension braces typically use 3-point leverage systems wherein the brace includes supports engaging the sternum or the sub-clavicula region and the pelvic and pubic body region together with a support engaging the back in the lumbar and low thoracic region. They have proven effective in the treatment of vertebra problems such as compression fractures.

Even though the prior art hyperextension braces are working in principle, they may be improved in certain respects. For example the connections between different members of the brace often include screws and bolts, requiring tools to adjust the size of the brace. Typically they are made of metal parts which not only may be heavy but interfere with X-ray equipment.

An object of the present invention is to provide a hyperextension brace which is easy to fit on a patient without requiring any tools. Another object is to provide a hyperextension brace which do not interfere with X-ray equipment.

SUMMARY OF THE INVENTION

The invention provides a frame for a hyperextension brace comprising: a sub-clavicula support, and a pelvic and pubic support connected by side members.

According to the invention, the height of the side members is adjustable by means of a non-rotational telescopic and lockable connection.

Preferably, the upper sub-clavicula support is connected by means of a turnbuckle screw arrangement to the side members.

The frame may be made of composite material, suitably a polymer reinforced by glass fibre and/or carbon fibre.

The invention is defined in claim 1, while embodiments are set forth in the dependent claims.

BRIEF DESCRIPTION OF THE DRAWINGS

The invention will be described in detail below with reference to the accompanying drawings which:

FIG. 9 is an outer perspective view of a buckle, and

FIG. 10 is an inner perspective view of the buckle.

DETAILED DESCRIPTION OF PREFERRED EMBODIMENTS

An embodiment of the hyperextension brace frame in accordance with the present invention is shown in the figures. Basically, the brace comprises a main frame as shown in FIGS. 1-4 and a posterior band with a dorsal pad shown in FIG. 8. The working principle for treatment of patients using the brace is known from the prior art.

The main frame comprises an upper, sub-clavicular support 1 with pads 12 arranged to apply pressure on the sternum or sub-clavicular region of a patient. The upper support 1 is connected by means of upper and lower side members 3, 4 to a lower pelvic and pubic support 2 arranged to apply pressure on a pelvic and pubic area on a patient.

Figure 1:
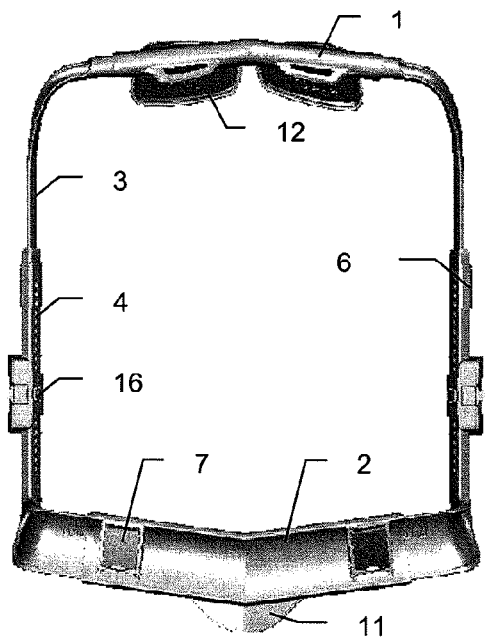
FIG. 1 is a front view of the main frame of the brace.
Figure 2:
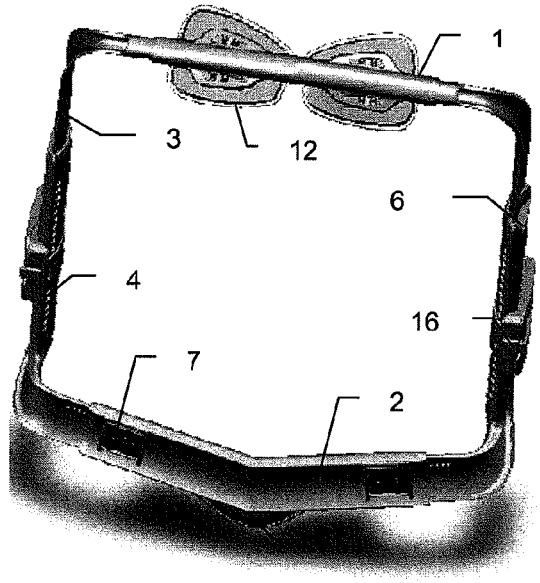
FIG. 2 is a perspective view from the front of the main frame.
Figure 3:
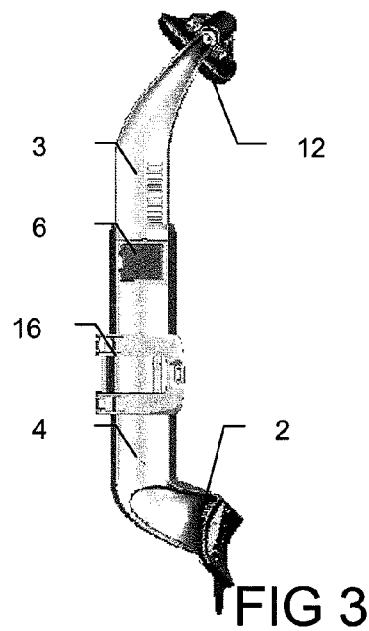
FIG. 3 is a side view of the main frame.
Figure 4:
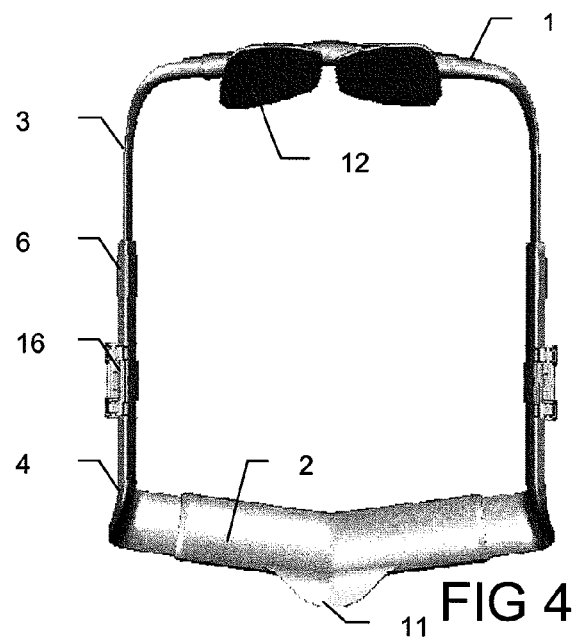
FIG. 4 is rear view of the main frame.

As may be seen from FIGS. 2 and 3, the side members 3, 4 project forward at their ends so that upper support 1 and lower support 2 are located forward of the side members 3, 4. Both the upper support 1 and lower support 2 are slightly curved or elliptically shaped for a comfortable fit on the patient.

Figure 5:
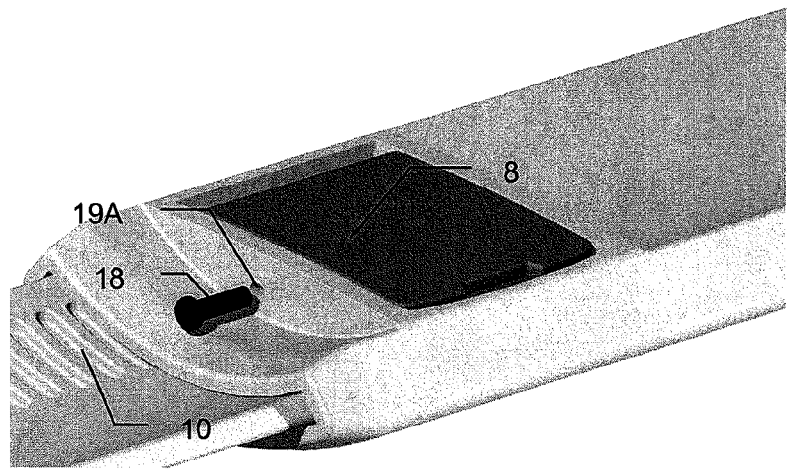
FIG. 5 is a cut-away view in perspective of the locking means in a closed position.
Figure 6:
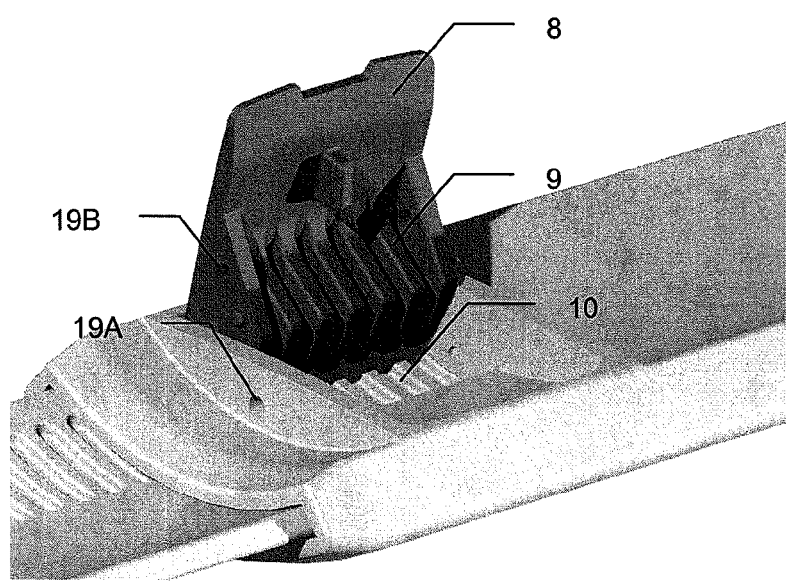
FIG. 6 is a cut-away view in perspective of the locking means in an open position.

With reference to FIGS. 5 and 6 the lower pubic support 2 is connected to the lower pubic side members 4 by means of locking means 7 provided at each side. The side members 4 are provided with integral side parts to be connected with the lower support 2. The side member 4 is slidable relative to the lower support 2 and lockable in a number of positions. Preferably, the side member 4 is more or less encircled by the support 2, like a male/female or telescopic connection, for structural stability. The outer or male element should engage at least the edges or other guiding portions of the inner or female element, so that the inner or female element is guided by the outer or male element when sliding, and held securely in place with respect to translation and rotation when locked. In FIGS. 5 and 6 the outer or male element completely encircles the inner or female element, but the outer or male element may be open at one side so that the outer or male element encircles the inner or female element with a C-shape. In this specification a connection with such a function is referred to as a non-rotational telescopic connection, whether completely encircling or not.

The upper and lower side members 3, 4 are also coupled together by means of a similar locking means 6. The locking means 6 may be of a design identical to that of the locking means 7.

One embodiment of the locking means is shown in FIGS. 5 and 6. The locking means comprises a lug 8 which is pivotably attached to one of the connected elements, such as the lower support 2 and the lower elements 4 of the side members 3. The underside of the lugs is provided with teeth 9, which may be brought into engagement in recesses 10 provided in the other of the connected elements. The width of the frame at the lower support 2, and the height of the side members 3, 4, may be adjusted by lifting the lug 8 as shown in FIG. 6, extending or retracting the elements relative to each other and then pushing down the lug 8 as shown in FIG. 5.

A locking pin 18 may be inserted in holes 19A, 19B in the connected element and lug element 8, respectively, to secure the lug in the locked position.

As is also shown in FIGS. 5, and 6, the elements of the frame are preferably curved in the transverse direction for improved bending resistance.

In the figures the lower pelvic and pubic support is provided with a symphysis pad 11. For best support, the lower pelvic and pubic support should be positioned just over (on top of) the groin line. In this way the symphysis pad 11 should cover the pubis ischiadicum (=symphysis). Preferably, the lower support member is provided in two versions, one with the symphysis pad 11 and one without it. It will be appreciated from the discussion above, that it is easy to release the whole lower pubic support 2 and change between the two versions, if desired.

Figure 7:
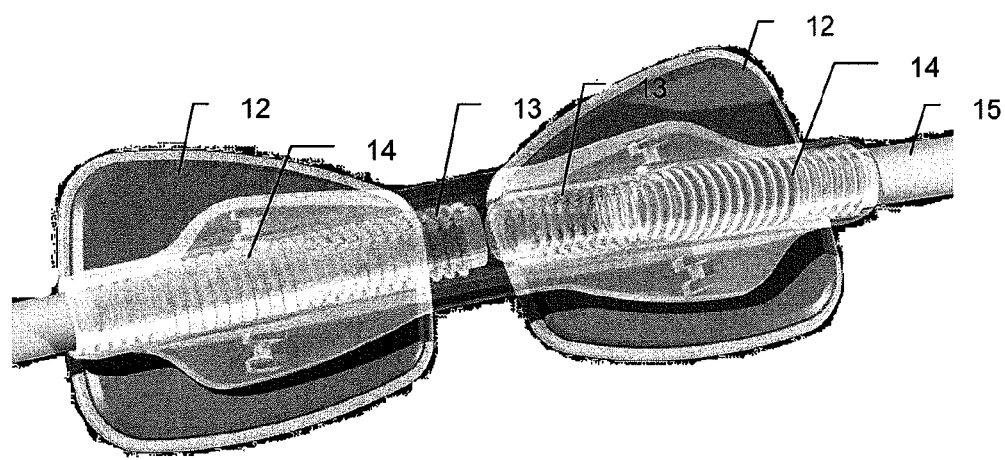
FIG. 7 is a transparent view of the upper support with pads and threads shown.

In principle, the same type of sliding and lockable locking means may be provided for the upper sub-clavicular support 1. However, a preferred embodiment of a sliding and lockable locking means for the upper support is shown in FIG. 7. The sub-clavicular support 1 comprises two sub-clavicular pads 12 placed at opposite ends of the slightly angled support 1. The support carries internal threads 13 for co-operation with external threads 14 provided on horizontal parts 15 integral with the side members 3. The threads have opposite pitches resulting in that the upper support 1 may be extended and retracted as a turnbuckle screw. If the support 1 is rotated in one direction, suitably towards the body, the side elements are pulled together, and if the support 1 is rotated in the other direction, away from the body, the side members 3 are separated.

Since the support 1 is slightly angled rotating it results in bending of the side members which causes a resisting force. The angles of the sub-clavicular support and side members 3 are selected such that there is a rest position which is the position shown in the figures. This position corresponds to a typical comfortable position for the patient with the pads substantially flat against the patient's body. However, only a small force is required to rotate the sub-clavicular support 1 over a small angle around the rest position. This results in that the pads will adjust themselves to small variations in the anatomy of the patient around the claviculae and rib-cage where the pads 12 are resting. For best support, the sub-clavicula pads 12 should be positioned approximately 2 cm below the claviculae.

For adjusting the width of the upper support 1, one or more whole turns) (360° in either direction are required. The resisting force of the side members is not very great and it can easily be done manually. The pitch of the threads 13, 14 is selected so that one turn results in approximately 7 mm extension or retraction. When the 12 pads rest against the patient's body, the width of the upper support 1 is locked.

Figure 8:
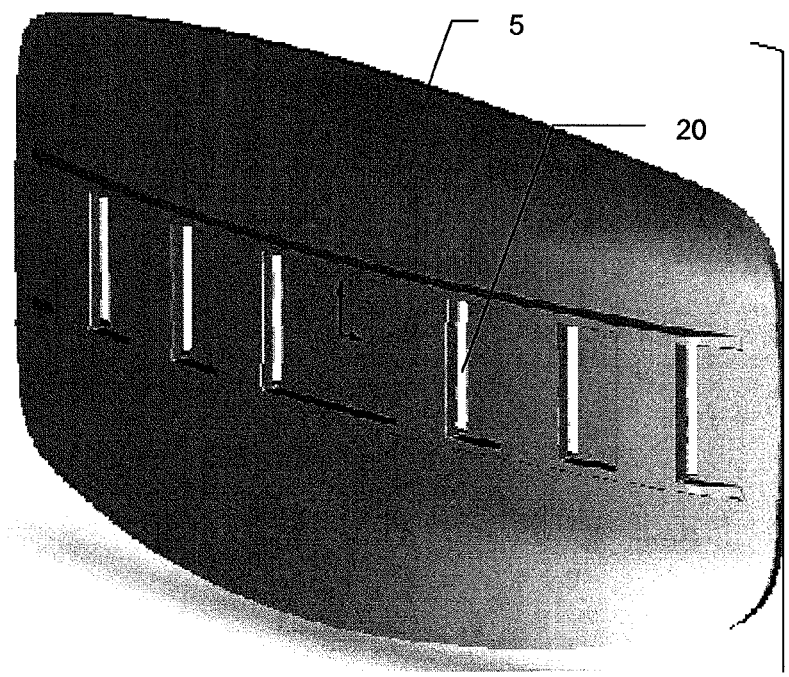
FIG. 8 is a perspective view of the dorsal pad.

FIG. 8 shows a dorsal pad 5. For clarity the posterior band is omitted so as not to obscure the view. The dorsal pad 5 has a generally oval shape to be comfortably placed at the lumbar and low thoracic region of the patient. The posterior band is threaded through holes 20 in the dorsal pad 5 and attached to the side members 3 at a distance from the lower support 2. The inner side facing the back of the patient is substantially smooth.

FIG. 9 shows a buckle 16 for tightening and releasable fastening the waist band. Preferably there is one buckle at each side for symmetry reasons, so that it is easier to centre the dorsal pad 5 on the body. Each buckle 16 has a leverage mechanism 17 taking up a certain amount of slack of the band when the buckle is fastened. The leverage mechanism 17 is pivotally attached at one side and may be closed and opened at the other side. Suitably, the length of the leverage mechanism 17 is around 50 mm so that each buckle takes up around 100 mm of slack. The length of the posterior band may be adjusted at the dorsal pad 5 or the buckles with conventional means (not shown).

The position of the connection to the side members is preferably adjustable in height as shown in FIG. 10. Recesses 21 are provided in the lower side members 4. Each buckle 16 has a resilient tongue 22 which releasably can snap into the recesses 21 to lock the buckle in position at a suitable height.

Preferably, the whole brace is manufactured of a non-metal, non-magnetic, and light-weight material. For instance, the main frame may be made of a polymer which may be reinforced by glass and/or by carbon fibre. Such parts may be injection moulded. Also the buckles 16 are made of plastic and the posterior band is made of synthetic or natural fabric.

The present invention provides a hyperextension brace which is handy and economic and may be fitted without requiring any tools. Due to choice of material the brace is light-weight, easy to clean and does not interfere with equipment sensitive to electric or magnetic interference. The material may be thermoplastic enabling adjustment by heating elements and adapting the shapes. The shape of the frame may be adjusted within wide ranges and independently at the sides, and at the upper and lower supports which results in that one size is sufficient to cover a full range of sizes of patients.

In the description and drawings specific embodiments have been shown in detail as embodiments of the invention. The scope of the invention is only limited by the claims below.

The invention claimed is:

1. A frame for a hyperextension brace comprising:
    a sub-clavicula support, and a pelvic and public support connected by side members, wherein
    the height of the side members, and thus the height of the frame, is adjustable by a non-rotational telescopic and lockable connection, whereby the subclavicula support is connected by a turnbuckle screw arrangement to the side members.

2. A frame for a hyperextension brace according to claim 1, wherein the turnbuckle screw arrangement is angled.

3. A frame for a hyperextension brace according to claim 2, wherein the pubic support is connected to the side members by a sliding and lockable connection at each side.

4. A frame for a hyperextension brace according to claim 3, wherein a posterior band is connected to each of the side members by buckles.

5. A frame for a hyperextension brace according to claim 2, wherein the connections comprise locking elements having engageable teeth and recesses.

6. A frame for a hyperextension brace according to claim 2, wherein a posterior band is connected to each of the side members by buckles.

7. A frame for a hyperextension brace according to claim 2, wherein the frame essentially is made of composite material.

8. A frame for a hyperextension brace according to claim 1, wherein the width of the pelvic and pubic support is adjustable by a non-rotational telescopic and lockable connection.

9. A frame for a hyperextension brace according to claim 8, wherein the pubic support is connected to the side members by a sliding and lockable connection at each side.

10. A frame for a hyperextension brace according to claim 8, wherein a posterior band is connected to each of the side members by buckles.

11. A frame for a hyperextension brace according to claim 8, wherein the frame essentially is made of composite material.

12. A frame for a hyperextension brace according to claim 1, wherein the connections comprise locking elements having engageable teeth and recesses.

13. A frame for a hyperextension brace according to claim 12, wherein a posterior band is connected to each of the side members by buckles.

14. A frame for a hyperextension brace according to claim 12, wherein the frame is essentially made of composite material.

15. A frame for a hyperextension brace according to claim 1, wherein a posterior band is connected to each of the side members by buckles.

16. A frame for a hyperextension brace according to claim 15, wherein each buckle is provided with a leverage mechanism taking up slack of the band.

17. A frame for a hyperextension brace according to claim 16, wherein the posterior band is connected to each of the side members at positions adjustable in height.

18. A frame for a hyperextension brace according to claim 1, wherein the frame essentially is made of composite material.

19. A frame for a hyperextension brace according to claim 18, wherein the composite material is a polymer reinforced by at least one of the group comprising glass fiber and carbon fiber.

20. A frame for a hyperextension brace according to claim 19, wherein the main parts of the pelvic and pubic support and the side members are curved in their respective transverse directions.

* * * * *